United States Patent
Lam (12) 
(10) Patent No.: US 6,539,984 B2
(45) Date of Patent: Apr. 1, 2003

(54) METHOD AND APPARATUS FOR FORMING A HEART VALVE WIREFORM

(75) Inventor: Hung Ly Lam, Norco, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 09/903,974

(22) Filed: Jul. 12, 2001

(65) Prior Publication Data

US 2002/0035860 A1 Mar. 28, 2002

Related U.S. Application Data (60) Provisional application No. 60/217,820, filed on Jul. 12, 2000.

(51) Int. Cl.$^7$ ................................................ B21F 1/04
(52) U.S. Cl. ................................................ 140/71 R
(58) Field of Search ................................ 140/71 R, 89, 140/90; 72/298

(56) References Cited

U.S. PATENT DOCUMENTS

| | | | |
|---|---|---|---|
| 2,188,407 A | * | 1/1940 | Horton .................... 140/90 |
| 2,715,424 A | * | 8/1955 | Fante et al. ............. 140/71 R |
| 3,608,097 A | | 9/1971 | Bellhouse et al. |
| 4,106,129 A | | 8/1978 | Carpentier et al. |
| 4,501,030 A | | 2/1985 | Lane |
| 4,798,073 A | | 1/1989 | Dischler |
| 6,296,662 B1 | | 10/2001 | Caffey |

FOREIGN PATENT DOCUMENTS

DE 4310773 A1 10/1994

* cited by examiner

*Primary Examiner*—Lowell A. Larson
(74) *Attorney, Agent, or Firm*—John Christopher James; Guy L. Cumberbatch

(57) ABSTRACT

A system and method for forming a three-dimensional wireform for heart valves from a two-dimensional starting shape. The wireform has multiple arcuate cusps and oppositely directed commissure tips therebetween, the cusps and commissure tips being oriented generally in a tube about an axis. The two-dimensional wire has three cusps and two commissure tips, with two free ends having bent segments. The wireforming system and process holds the commissure tips, or one commissure tip and one bent segment, and forms the cusp therebetween. The wire is held by two axially-parallel mandrels and cooperating clamps which axially rotate and move toward one another. A forming surface on each mandrel bends one half of the cusp, the forming surfaces being mirror images of one another. The forming surface has a complex curvature specifically designed to shape a particular size of wireform into a desired final three-dimensional shape. After bending all the cusps, the free ends of the wire are joined, such as with a tubular crimp, and the wireform assembled into a tissue-type heart valve.

17 Claims, 10 Drawing Sheets

METHOD AND APPARATUS FOR FORMING A HEART VALVE WIREFORM

RELATED APPLICATION

The present application claims priority under 35 U.S.C. §119 to U.S. Provisional Application No. 60/217,820, filed Jul. 12, 2000 under the same title.

FIELD OF THE INVENTION

The present invention relates generally to medical devices, and more particularly to a method and apparatus for forming a three-dimensional wireform for use in heart valves.

BACKGROUND OF THE INVENTION

Two primary types of heart valve replacements or prostheses are known. One is a mechanical-type heart valve that uses a ball and cage arrangement or a pivoting mechanical closure to provide unidirectional blood flow. The other is a tissue-type or "bioprosthetic" valve which is constructed with natural-tissue valve leaflets which function much like those in a natural human heart valve, imitating the natural action of the flexible leaflets that form commissures to seal against each other and ensure the one-way blood flow. In tissue valves, a whole xenograft valve (e.g., porcine) or a plurality of xenograft leaflets (e.g., bovine pericardium) provide occluding surfaces that are mounted within a surrounding stent structure.

In both types of bioprosthetic valves, an elastic wireform, typically metal, provides internal valve support for the flexible leaflets. The wireform has a three-dimensional shape, with a plurality (typically three) of large radius cusps supporting the cusp region of the leaflets of the bioprosthetic tissue (i.e., either a whole valve or three separate leaflets). The free ends of each two adjacent cusps converge somewhat asymptotically to form upstanding commissures that terminate in tips, each being curved in the opposite direction as the cusps and having a relatively smaller radius.

The wireform is typically a non-ferromagnetic metal such as Elgiloy that possesses substantial elasticity. A common method of forming the wireform is to bend a wire into a flat (2-dimensional) undulating pattern of the alternating cusps and commissures, and then roll the flat pattern into a cylinder using a cylindrical roller. The free ends of the resulting 3-dimensional shape, typically in the asymptotic region of the cusps, are then fastened together using a tubular crimp. Because of the configuration (i.e., curvatures, circumferential arcs, axial lengths) of the alternating cusps and commissures, the elasticity (springback) of the material, and the required overall diameter of the 3-dimensional wireform, the free ends do not meet after the rolling step. Rather, there is some separation, and the wire must be constricted to a degree to bring the free ends together for crimping. As a result, the 3-dimensional wireform exhibits an outward spring bias in its final form, which may affect the dynamic response and fatigue life in the finished valve, and thus must be factored into the design. This additional design consideration is undesirable, and the performance of the valve may suffer from the wireform bias.

What is needed then is an improved method and apparatus for forming an unbiased three-dimensional heart valve wireform.

SUMMARY OF THE INVENTION

The present invention provides an apparatus for forming a three-dimensional wireform for use in a heart valve, comprising a first mandrel having a forming surface with a varying curvature, and a second mandrel having a forming surface with a varying curvature. The apparatus further includes a forming tool having clamps for cooperating with the mandrels and rigidly holding a two-dimensional wire and displacing the forming surfaces of the mandrels with respect to one another to bend the wire into a three-dimensional shape. The forming tool may include first and second shafts arranged to rotate along parallel axes, with the mandrels having throughbores sized to receive the respective shafts, wherein rotation of the shafts causes the displacement of the forming surfaces of the mandrels. The forming tool may include a linear slide for translating one of the shafts in a direction perpendicular to the parallel axes, such that displacement of the forming surfaces of the mandrels includes translating one of the shafts and forming surface toward the other shaft and forming surface. Motors coordinated by a programmable controller desirably rotate the shafts and translating the one shaft.

In one embodiment, the two dimensional wire includes alternating arcuate cusps and commissure tips, and the clamps and mandrels cooperate to hold two of the commissure tips with one of the arcuate cusps therebetween, the forming surfaces therefore bending the arcuate cusp of the wire when displaced. Each clamp and mandrel may be disposed on a shaft, with either the mandrel or clamp arranged to slide along the shaft with respect to the other to alternately hold and release the wire between the clamp and mandrel. The two dimensional wire desirably includes alternating arcuate cusps and commissure tips, and each mandrel includes a channel and cross-bores opening to the channel. Further, each clamp may have a recess aligned with the channel, wherein a pair of pins are provided fitting in the crossbores and sized so that one of the commissure tips may be wrapped therearound, the pins projecting into the channel a distance that permits sliding of the mandrel into cooperation with the clamp such that the projections of the pins fit within the clamp recess and the commissure tip is retained between the channel and recess.

Another aspect of the invention is a subassembly for bending a wire for a heart valve wireform, the wireform having alternating arcuate cusps and arcuate commissure tips. The subassembly includes a pair of mandrels having forming surfaces that have non-cylindrical cross-sectional shapes. Each mandrel may include a throughbore and a keyway, and the subassembly further includes, for each mandrel, a shaft sized to fit within the throughbore having an axial groove, and a key sized to fit within the groove in the shaft and within the keyway and couple rotation of the shaft and mandrel. The subassembly may further include, for each mandrel, a clamp having a throughbore and a keyway sized to receive the shaft and key, respectively, and couple rotation of the shaft, mandrel and clamp. Each mandrel preferably has an axial channel on one side adjacent the forming surface, and the clamp has an external recess aligned with the channel, the subassembly further including a retaining pin projecting into the channel and sized to receive therearound one of the arcuate commissure tips of the two-dimensional wire, the commissure tip being retained by overlapping of the channel and recess.

A method for forming a three-dimensional wireform for use in a heart valve is also provided by the present invention. The method comprises:

bending a wire into a flat (2-dimensional) undulating pattern of the alternating cusps and commissures; and bending the flat pattern into a three dimensional shape using:

a pair of mandrels having forming surfaces that have non-cylindrical cross-sectional shapes.

The method may be accomplished using a forming tool having clamps for cooperating with the mandrels and rigidly holding a two-dimensional wire, wherein the method includes displacing the forming surfaces of the mandrels with respect to one another to bend the wire into a three-dimensional shape. The forming tool desirably has first and second shafts arranged to rotate along parallel axes, and the mandrels have throughbores sized to receive the respective shafts, wherein the method further includes rotating the shafts to cause the displacement of the forming surfaces of the mandrels. Additionally, the forming tool preferably includes a linear slide for translating one of the shafts in a direction perpendicular to the parallel axes, and the displacement of the forming surfaces of the mandrels further includes translating one of the shafts and forming surface toward the other shaft and forming surface. Rotation of the shafts and translation of the one shaft is desirably carried out using motors and a programmable controller. The method desirably involves holding two of the commissures of the wire with a cusp therebetween and using the pair of mandrels to bend one cusp at a time.

DESCRIPTION OF THE PREFERRED EMBODIMENTS

Figure 1:
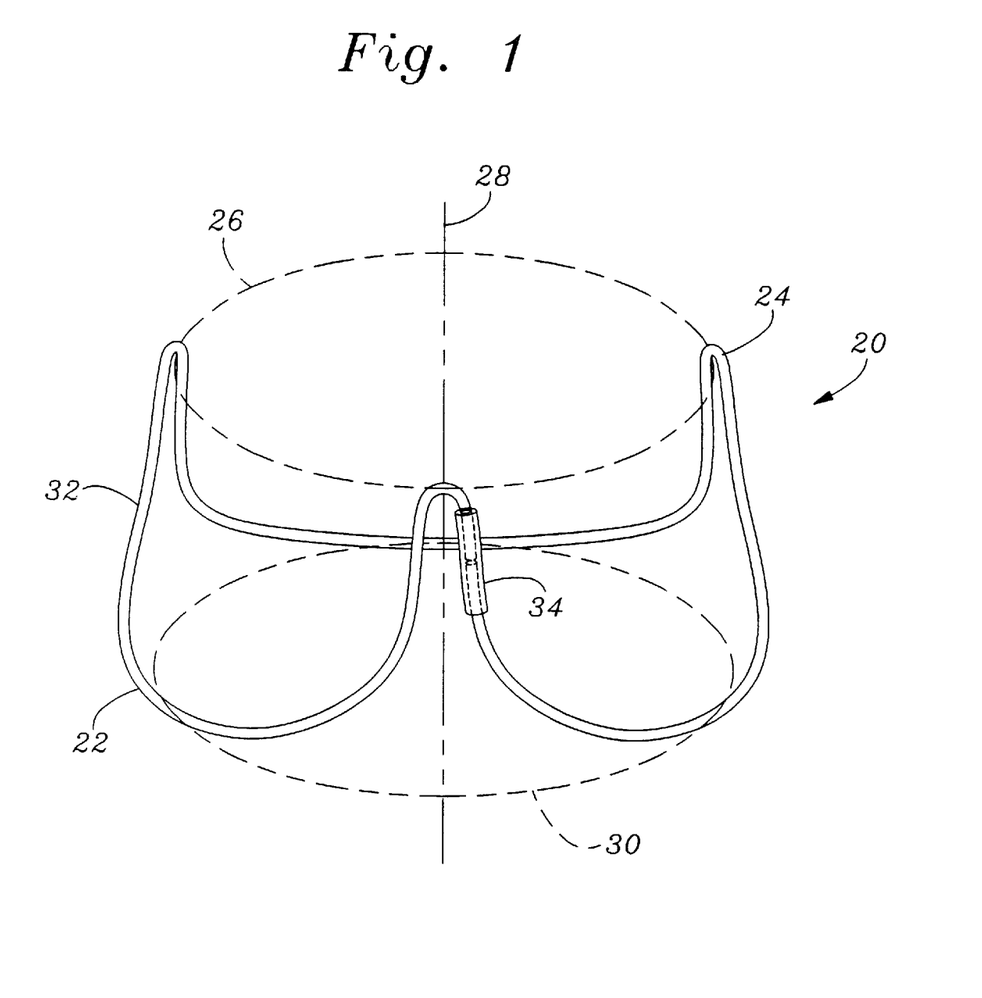
FIG. 1 is a perspective view of a wireform used in the construction of tissue-type heart valves and formed by the systems and methods of the present invention.

The present invention provides an improved wireform, forming apparatus and method as described herein and shown in the accompanying drawings. A finished wireform 20 is seen in FIG. 1 and includes alternating and oppositely-directed cusps 22 and commissure tips 24. The commissure tips 24 lie in a plane on an imaginary circle 26 about an axis 28. Likewise, the apices of the arcuate cusps 22 lie in a plane on an imaginary circle 30 about the axis 28. Gradual bends 32 define transitions between the commissure tips 24 and each of the adjacent cusps 22. These bends 32 permit the imaginary circles 26, 30 to have the same diameter.

The wireform 20 thus defines a substantially cylindrical volume therewithin, with the wireform 20 lying entirely in the tubular projection between the imaginary circles 26, 30. Of course, other volumes may be defined by the wireform 20 wherein the imaginary circle 26 is smaller or larger than imaginary circle 30. For example, the apices of the arcuate cusps 22 may be provided outward from the commissure tips 24 so the wireform 20 defines a frusto-conical volume therewithin. The three-dimensional shape of the wireform 20 is specifically designed to support the leaflets of the prosthetic heart valve, and close tolerances are important to ensure high performance and durability of the valve. It will thus be understood that the relatively complex contours of the wireform 20 must be controlled to a high degree of precision to result in the desired three-dimensional shape.

A crimp 34 holds together the two free ends of the wire used to form the wireform 20. The crimp 34 is typically a short tubular metallic member that is compressed about the free ends and holds them by friction.

In accordance with the present invention, the wireform 20 is formed by:

bending a wire into a flat (2-dimensional) undulating pattern of the alternating cusps and commissures; and bending the flat pattern into a three dimensional shape using:

a first mandrel having a forming surface with a varying curvature;

a second mandrel having a forming surface with a varying curvature; and     a forming tool having clamps for cooperating with the mandrels and rigidly holding the two-dimensional wire and displacing the forming surfaces of the mandrels with respect to one another to bend the wire into a three-dimensional shape.

As will be described in greater detail below, the forming surfaces of the mandrels are specifically designed to create a resultant tubular shaped wireform, taking into account the varying curvatures of the cusps and commissures and the springback property of the material. The wireform material is desirably Elgiloy.

Figure 2:
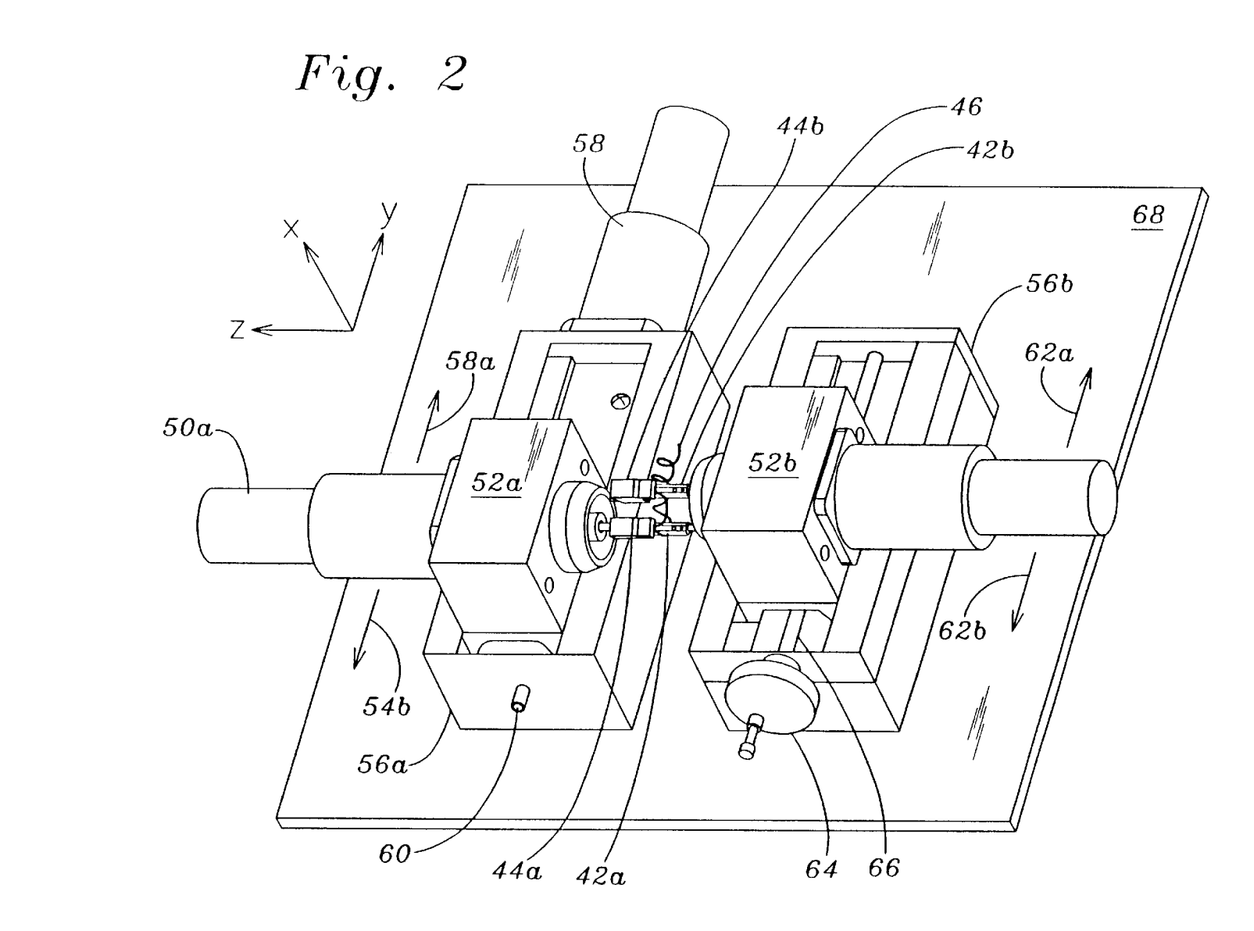
FIG. 2 is a perspective view of a system of the present invention for forming the three-dimensional wireforms of FIG. 1.
Figure 3:
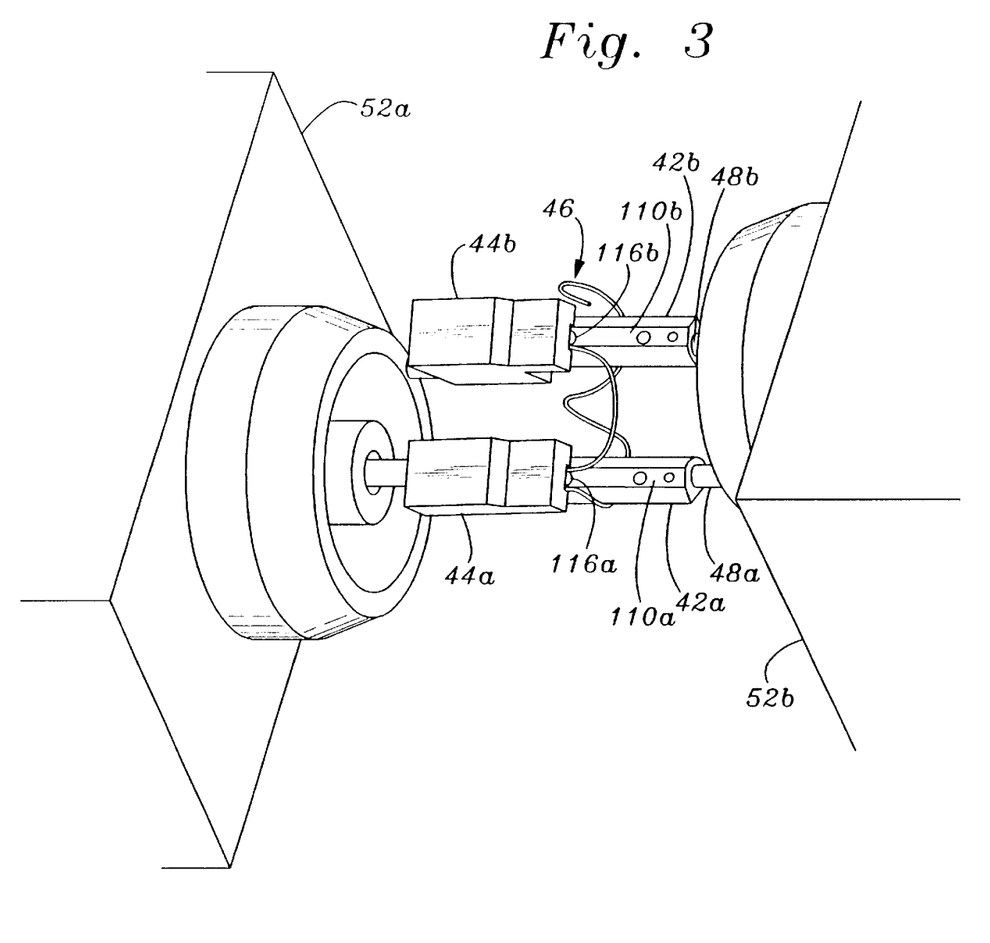
FIG. 3 is an enlarged perspective view of the system of FIG. 2 showing the last step in the bending process of a wireform of the present invention.

A tool or system 40 for forming the wireform 20 is shown in FIG. 2 and includes two mandrels 42a, 42b each of which cooperates with a clamp 44a or 44b to hold and bend a wire 46. The wire 46 is seen in FIG. 2 in a two-dimensional configuration with the cusps and commissure tips having previously been formed therein. FIG. 2 thus depicts the system 40 and wire 46 just prior to a first step in forming the three-dimensional wireform 20 seen in FIG. 1. In FIG. 3, the cooperating mandrels 42a, 42b and clamps 44a, 44b are seen enlarged holding the now three-dimensional wire 46 just prior to a third step in the wireforming process, which process will be described in greater detail below.

Each mandrel/clamp subassembly rotates about a longitudinal axis centered in a shaft 48a or 48b (FIG. 3). As seen in FIG. 2, a first stepper motor 50a axially rotates one shaft 48a, and a second stepper motor 50b axially rotates the second shaft 48b. Both the motors 50a, 50b and shafts 48a, 48b are mounted, respectively, with respect to a housing 52a, 52b. The first housing 52a (and thus first mandrel/clamp/shaft subassembly) translates in the directions of arrows 54a, 54b along the linear slide of a first base frame 56a when driven by a third stepper motor 58 and lead screw 60. The second housing 52b (and thus second mandrel/clamp/shaft subassembly) translates in the directions of arrows 62a, 62b along the linear slide of a second base frame 56b when driven by a manual adjust knob 64 and lead screw 66. The first and second base frames 56a, 56b are positionally fixed with respect to one another, such as on a table or platen 68. It should be understood that a programmable control system (not shown) desirably coordinates the movements of the motors 50a, 50b and 58.

For purpose of orientation and discussion, a system of coordinate axes is shown in the upper left hand portion of FIG. 2. The shafts 48a, 48b align and rotate about axes parallel to the Z-axis, while the first and second housings 52a, 52b translate parallel to the Y-axis. The wire 46 initially exists in a two-dimensional form in the Y-Z plane.

Figure 4A:
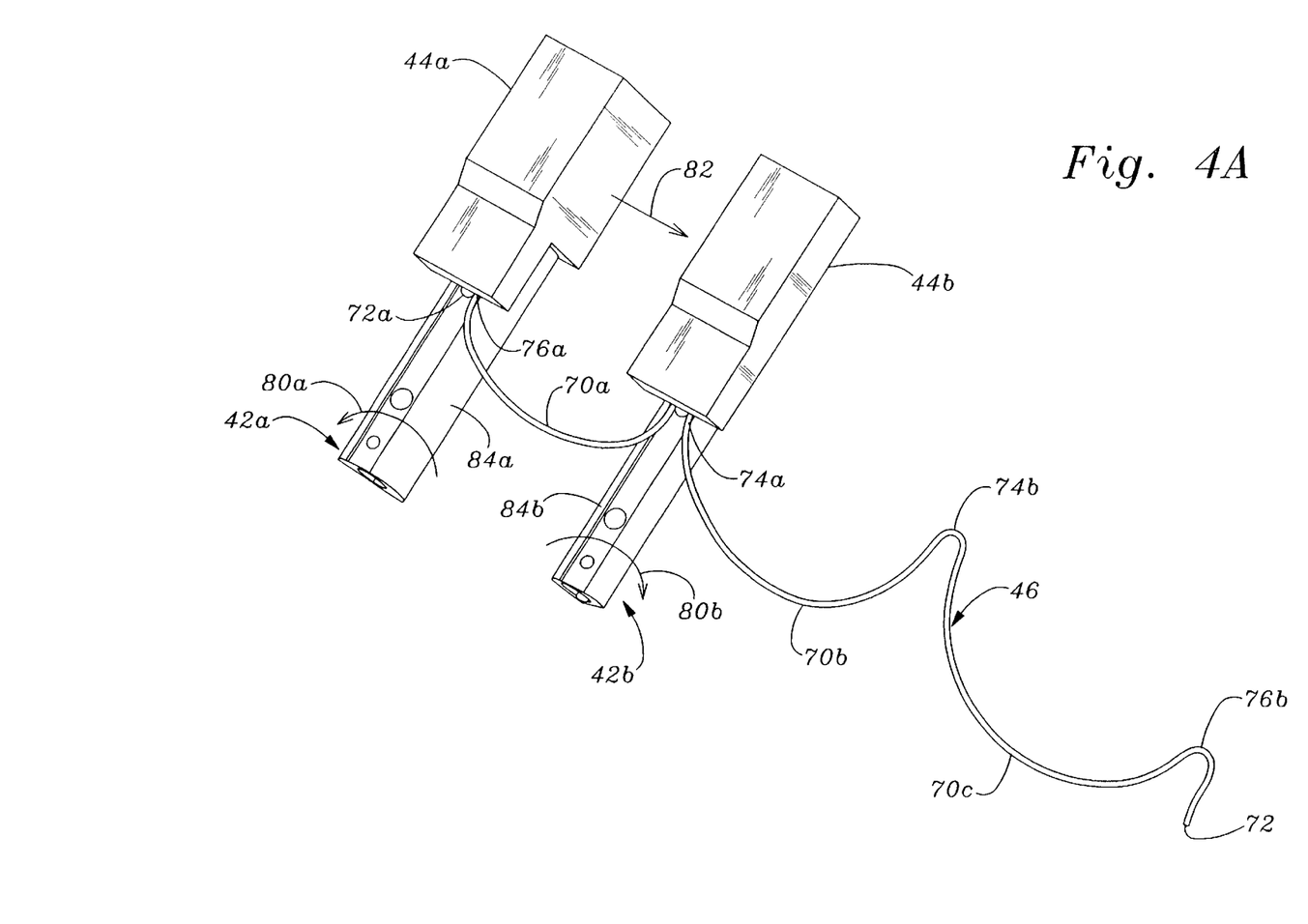
FIGS. 4A–4C are perspective views of a mandrel and clamp subassembly of the system of FIG. 2 showing three steps in the bending process of a wireform.
Figure 4B:
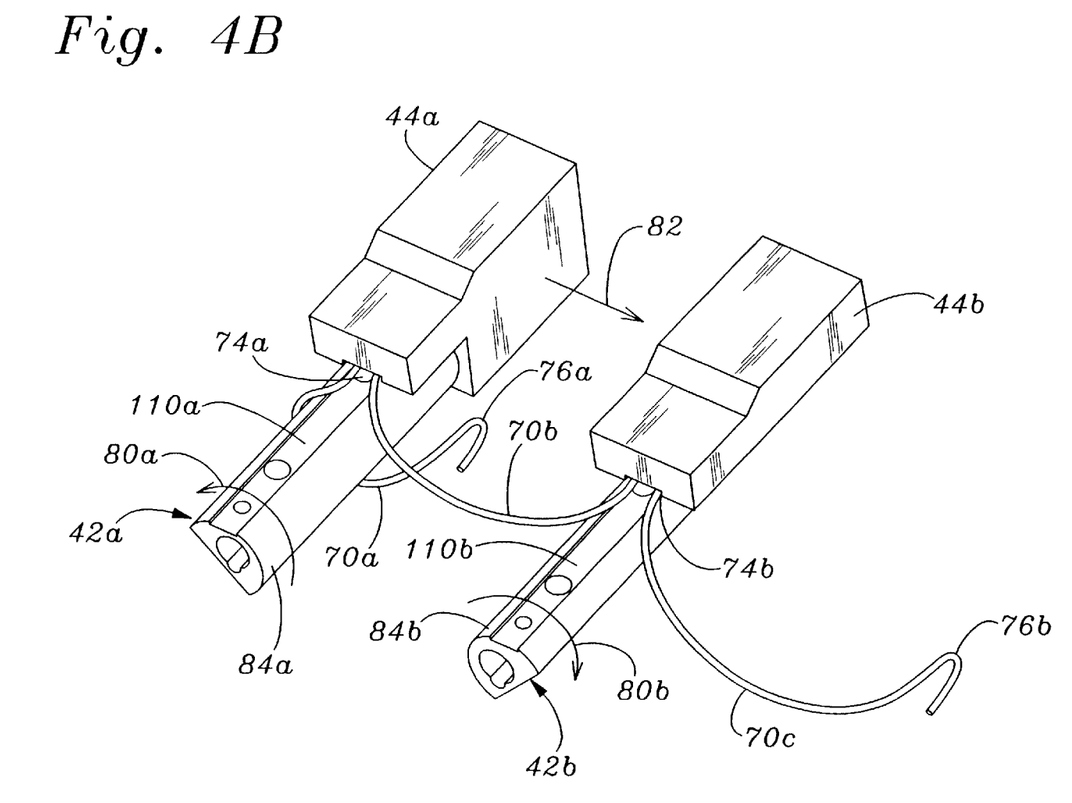
Figure 4C:
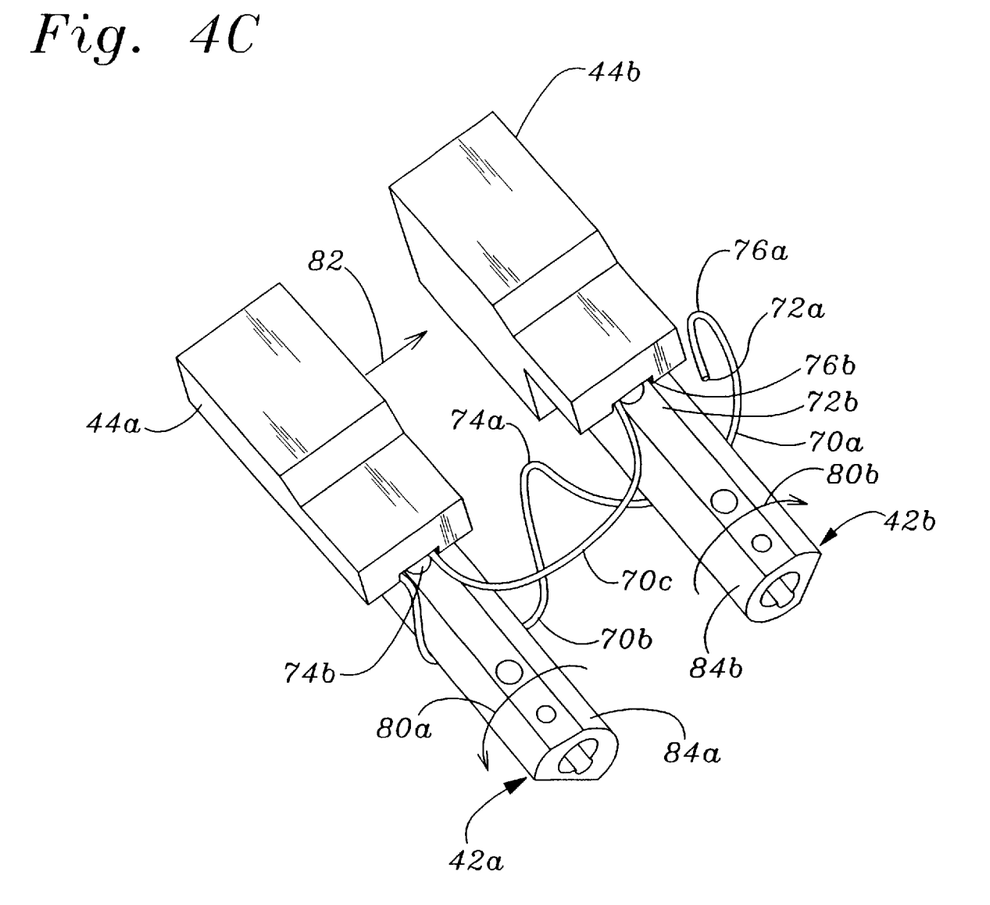

FIGS. 4A–4C illustrate in isolation the two mandrel/clamp subassemblies and the wire 46 just prior to the three wireforming process steps. The wire 46 in its two-dimensional form in FIG. 4A has three arcuate cusps 70a, 70b, 70c and two free ends 72a, 72b. A first arcuate commissure tip 74a separates the first and second adjacent cusps 70a, 70b while a second arcuate commissure tip 74b separates the second and third adjacent cusps 70b, 70c. Each free end 72a, 72b respectively terminates a short generally straight segment of the wire 46 adjacent a bent segment 76a, 76b that may form the third commissure, as will be explained below.

The wire 46 is initially held in the position shown in FIG. 4A, with the first bent segment 76a firmly held between the first mandrel 42a and clamp 44a, and the first arcuate commissure tip 74a firmly held between the second mandrel 42b and clamp 44b. The first step in the wireforming operation comprises moving the mandrel/clamp subassemblies in the direction of arrows 80 and 82 to bend the first arcuate cusp 70a. Specifically, upon actuation of the first and second stepper motors 50a, 50b and shafts 48a, 48b (see FIGS. 2 and 3), the mandrel/clamp subassemblies rotate in opposite directions, as depicted by the arrows 80a, 80b. At the same time, the third stepper motor 58 and lead screw 60 translates the housing 52a (FIG. 2), causing the first mandrel/clamp subassembly to translate in the direction of arrow 82, toward the second mandrel/clamp subassembly. Each mandrel 42a, 42b defines a forming surface 84a, 84b that bends the first arcuate cusp 70a into a specific shape as the mandrels rotate and travel toward one another. At a predetermined point, such as when the clamps 44a, 44b contact each other, the movement stops and the wire 46 is released from the system 40.

The next step in the wireforming process begins as shown in FIG. 4B, with the first arcuate commissure tip 74a firmly held between the first mandrel 42a and clamp 44a, and the second arcuate commissure tip 74b firmly held between the second mandrel 42b and clamp 44b. The mandrel/clamp subassemblies again move in the direction of arrows 80 and 82 to bend the second arcuate cusp 70b. The first arcuate cusp 70a is seen bent in three-dimensions behind the first mandrel 42a.

The last step in the wireforming process begins as shown in FIG. 4C, with the second arcuate commissure tip 74b firmly held between the first mandrel 42a and clamp 44a, and the second bent segment 76b firmly held between the second mandrel 42b and clamp 44b. The mandrel/clamp subassemblies again move in the direction of arrows 80 and 82 to bend the third arcuate cusp 70c. The first and second arcuate cusps 70a, 70b are seen bent in three-dimensions behind the mandrels 42a, 42b.

The 3-dimensional wireform shape maybe formed as described, although preferably the process involves first bending one of the outer cusps 70a or 70c in the flat wire 46, then bending the other outer cusp, and then the middle cusp 70b.

After the wire 46 is bent into its generally tubular form utilizing the system 40 of the present invention, one of the bent segments 76a or 76b is severed and the resulting severed free end is aligned with the remaining free end 72a or 72b. A coupling, such as the crimp 34 seen in FIG. 1, is installed to form the wireform 20.

Figure 5:
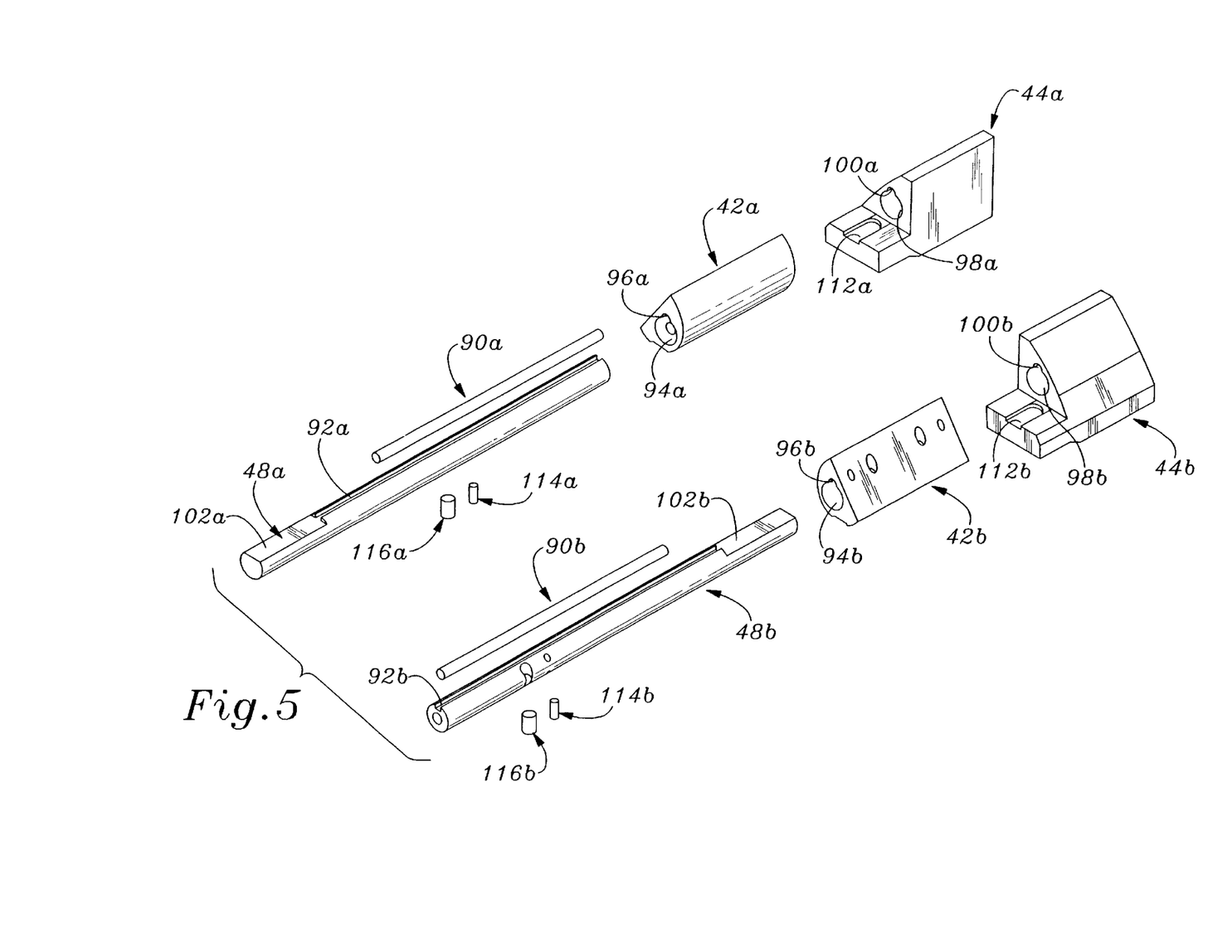
FIG. 5 is an exploded perspective view of dual mandrel, clamp and shaft subassemblies of the system of FIG. 2.

An exemplary embodiment of the main wireforming components will now be described with respect to the exploded perspective of FIG. 5, as well as the detailed views of FIGS. 6–8. FIG. 5 shows two parallel mandrel 42, clamp 44 and shaft 48 subassemblies, as used in the system 40 of FIG. 2. The subassemblies each further includes a shaft key 90a, 90b in the form of an elongated rod that fits within a complementary groove 92a, 92b in the respective shaft 48a, 48b. Each mandrel 42a, 42b has a throughbore 94a, 94b for receiving the shaft 48a, 48b, and a smaller keyway 96a, 96b in the sidewall thereof sized to receive the shaft key 90a, 90b. Likewise, each clamp 44a, 44b has a throughbore 98a, 98b and a smaller keyway 100a, 100b in the sidewall thereof, each for receiving the shaft 48a, 48b and shaft key 90a, 90b.

The aforementioned stepper motors 50a, 50b (FIG. 2) drive each shaft 48a, 48b via a flat 102a, 102b provided on one end. It will be noted that the flats 102a, 102b are on opposite ends in the drawing corresponding to the opposed configuration of the stepper motors 50a, 50b in the system 40. When the mandrel 42, clamp 44 and shaft 48 subassemblies are assembled and coupled to the stepper motors 50a, 50b, rotation of the shafts 48a, 48b also rotates the mandrels 42a, 42b and clamps 44a, 44b, by virtue of the shaft keys 90a, 90b and keyways 96a, 96b and 100a, 100b.

The manner in which the wire 46 is held in the system 40 as seen in FIG. 3 facilitates rapid change-out for the technician to speed up the three step process. Specifically, the mandrels 42a, 42b and clamps 44a, 44b slide with respect to one another along the shafts 48a, 48b, and the wire 46 is held therebetween when the two components are in axial abutment. This is seen in FIG. 3. Removal and repositioning of the wire 46 is accomplished by simply sliding either the mandrels 42a, 42b away from the clamps 44a, 44b (or visa versa), moving the wire 46, and again bringing the mandrels and clamps together.

As mentioned above, either a bent segment 76 and arcuate commissure tip 74 or two arcuate commissure tips 74 are held by the system. With reference to FIGS. 3, 5, and 6A–6F, these generally U-shaped features are retained between an axially disposed channel 110a, 110b on each mandrel 42a, 42b and a recess 112a, 112b on each clamp 44a, 44b. The channels 110a, 110b are perhaps best seen in FIG. 4B and in enlarged cross-section in FIG. 6D, while the recesses 112a, 112b are best seen in FIG. 5 and in the plan view of FIG. 7A. The side wall of the recesses 112a, 112b has a rounded inner end and a gradually tapered shape that corresponds to the shape of the commissure tips of the wire 46. Two pins, a smaller pin 114a, 114b and a larger pin 116a, 116b, fit within corresponding cross-bores (not numbered) in both the mandrels 42a, 42b and shafts 48a, 48b. The cross-bores in the mandrels 42a, 42b open along the centerline of the axial channels 110a, 110b and the pins 114a, 114b, and 116a, 116b have a length that projects beyond the floor of the channels. The commissure tips of the wire 46 hook around these pins 114a, 114b, and 116a, 116b, and the assembly is then slid into the recesses 112a, 112b of the clamps 44a, 44b. In this regard, the large pins 116a, 116b are visible in FIG. 3.

With reference to FIGS. 6A–6F, each mandrel 42 has an elongated body 120 arranged along an axis with parallel end faces 122, 124 normal to the axis. The throughbore 94 and keyway 96 open to the end faces 122, 124, and the exterior includes the aforementioned forming surface 84, the channel 110, and an angled side wall 126. with specific reference to the cross-section of FIG. 6C, the side wall 126 makes an angle α with a datum line A that is drawn parallel to the floor of the channel 110. The channel 110 has outwardly tapered side edges that desirably make an angle θ of about 90°. A second datum line B is shown extending perpendicular to datum line A and extending through the centerline of the channel 110. The linear projection of the side wall 126 intersects the datum line A at a point that is a distance C from the datum line B. The curvature of the forming surface 84 may be defined with respect to these datum lines A and B.

The following is a table that describes one exemplary forming surface 84 for a mandrel 42 that shapes a wireform to be used in 25 mm heart valves. Sixteen points on the surface 84 are given, with the continuous shape being derived by interpolating the curve between these points. Each point is given in inches from the intersection of the datum lines A and B. In this exemplary embodiment, and with reference to FIG. 6C, the angle α is about 52° and the distance C is about 0.173 inches. It should be understood that the specific shape of surface 84 depends not just on the heart valve size, but also on the desired axial height, the volume circumscribed by the wireform, and other such design parameters. In general, the forming surface 84 has a smaller radius of curvature adjacent to the channel 110, the curvature gradually smoothing out therefrom.

Figure 6A:
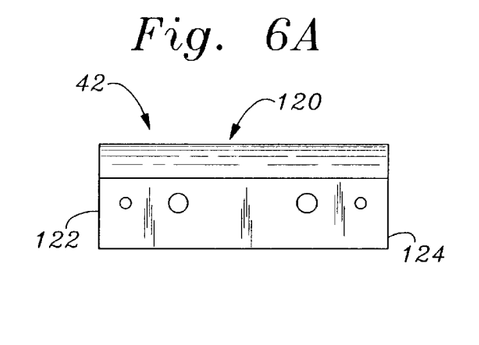
FIGS. 6A–6F are various views of the mandrel used in the system of FIG. 2.
Figures 6B, 6F:
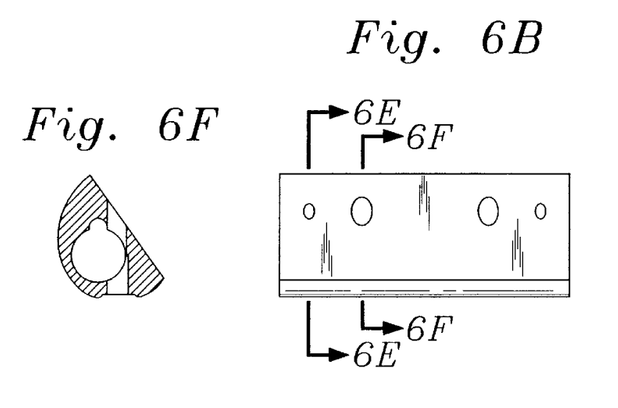
Figure 6C:
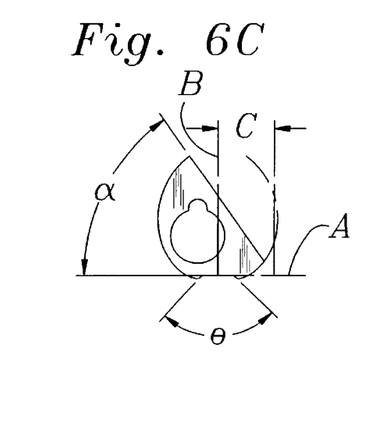
Figure 6D:
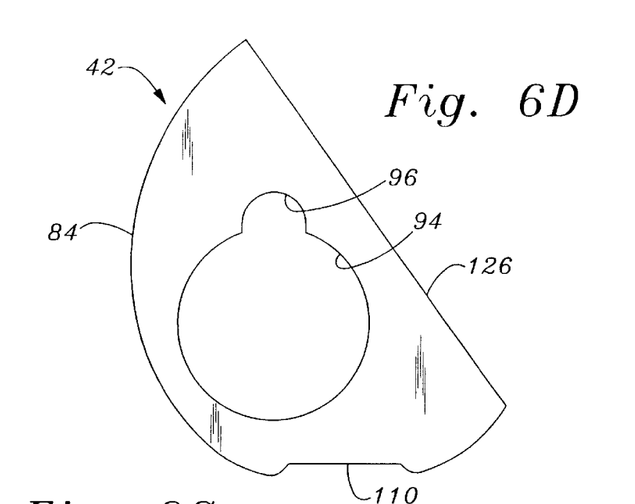
Figure 6E:
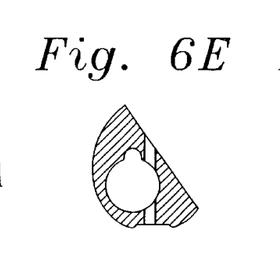
Figure 7A:
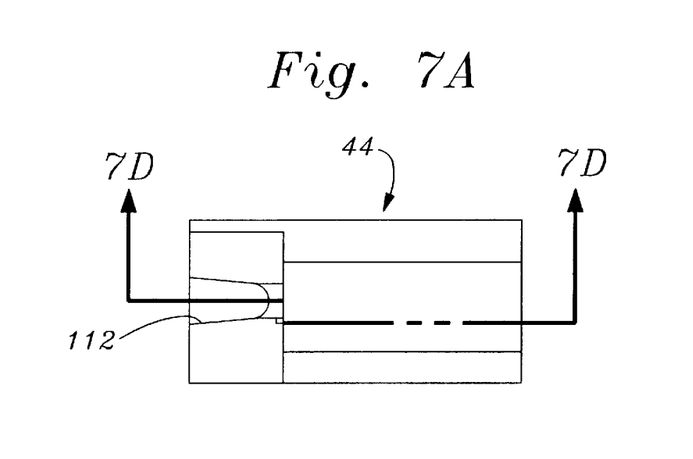
FIGS. 7A–7D are various views of the clamp used in the system of FIG. 2.
Figure 7B:
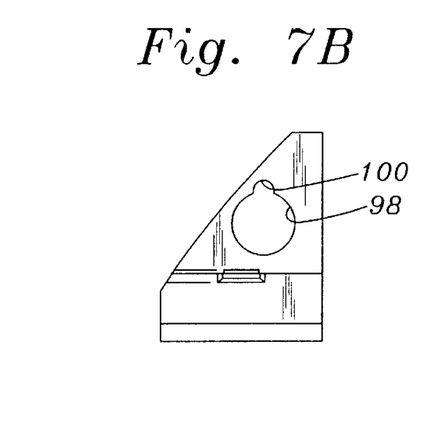
Figure 7C:
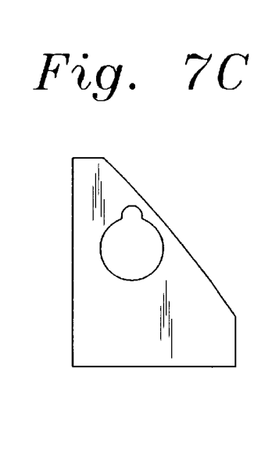
Figure 7D:
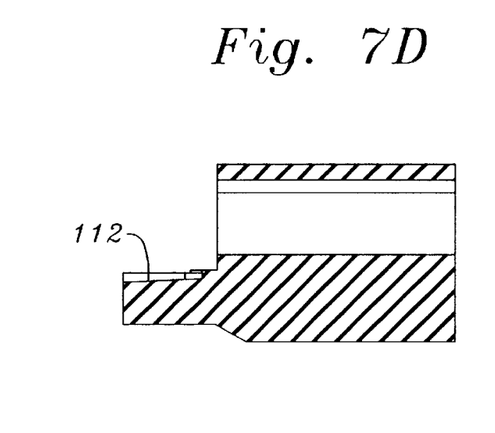
Figure 8A:
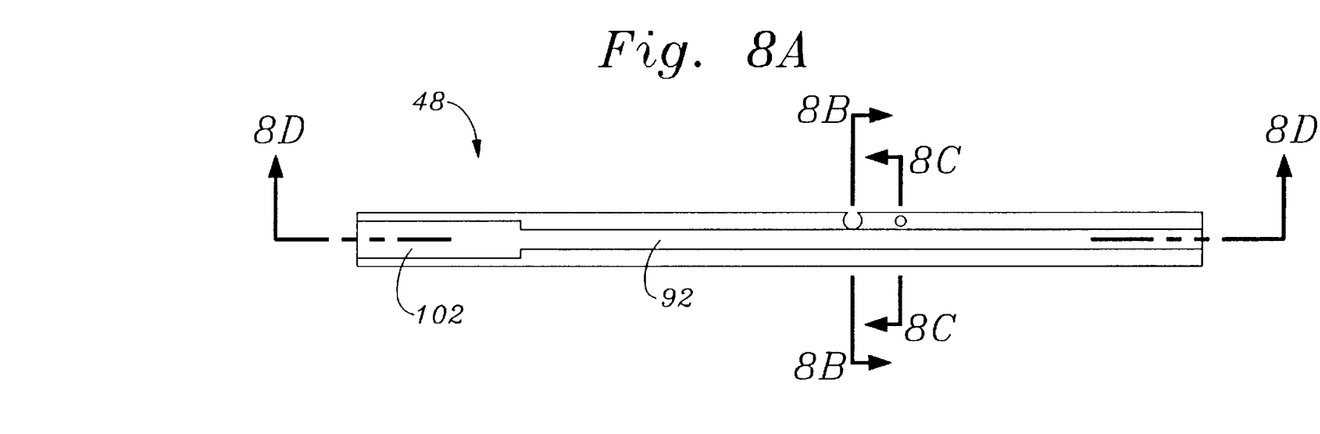
FIGS. 8A–8D are various views of a shaft used in the system of FIG. 2.
Figure 8B:
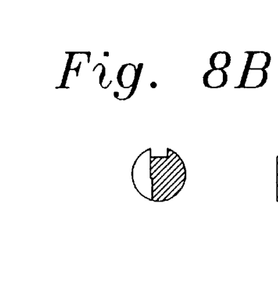
Figure 8C:
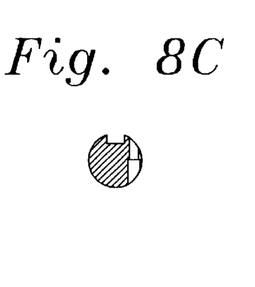
Figure 8D:
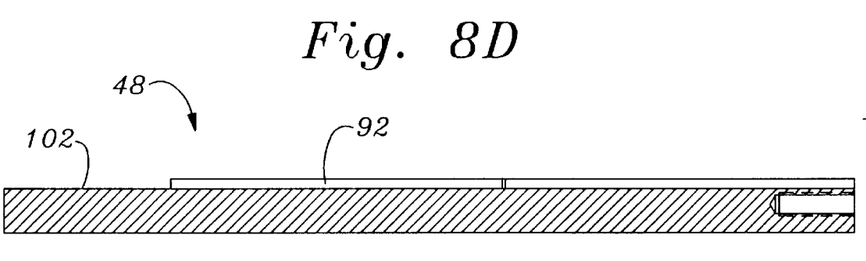

| I | B | A |
|---|---|---|
| 1 | .0583 | −.0101 |
| 2 | .0616 | −.0103 |
| 3 | .0705 | −.0086 |
| 4 | .0830 | −.0035 |
| 5 | .0978 | .0055 |
| 6 | .1138 | .0191 |
| 7 | .1297 | .0374 |
| 8 | .1443 | .0605 |
| 9 | .1563 | .0881 |
| 10 | .1643 | .1197 |
| 11 | .1673 | .1544 |
| 12 | .1642 | .1909 |
| 13 | .1544 | .2279 |
| 14 | .1379 | .2636 |
| 15 | .1148 | .2965 |
| 16 | .0795 | .3301 |

The generalized shape of the forming surface 84 can be obtained with an analysis of the final shape and character of the wireform 20. Parameters taken into account are the diameter of the wire 46, Young's modulus of elasticity of the wire material, and the yield stress. The spring back radius may also be a factor.

The end result is a wireform 20 that has very little bias or springback to resist coupling of the free ends. Because of the complex shape of the mandrel forming surfaces, the wire 46 is bent in a way that the final shape is generally tubular, with the cusps being bent to eliminate springback. This is in contrast to the relatively simple shape of a cylindrical mandrel which does not account for the complex contour of the wireform. Lower residual stresses in the wireform after coupling also may help extend the longevity of the heart valve itself.

It will be appreciated that the invention has been described hereabove with reference to certain examples or preferred embodiments as shown in the drawings. Various additions, deletions, changes and alterations may be made to the above-described embodiments and examples, and it is intended that all such additions, deletions, changes and alterations be included within the scope of the following claims.

What is claimed is:

1. An apparatus for forming a three-dimensional wireform for use in a heart valve, comprising:

a first mandrel having a forming surface with a varying curvature;

a second mandrel having a forming surface with a varying curvature; and a forming tool having clamps for cooperating with the mandrels and rigidly holding a two-dimensional wire and displacing the forming surfaces of the mandrels with respect to one another to bend the wire into a three-dimensional shape.

2. The apparatus of claim 1, wherein the forming tool includes first and second shafts arranged to rotate along parallel axes, the mandrels including throughbores sized to receive the respective shafts, wherein rotation of the shafts causes the displacement of the forming surfaces of the mandrels.

3. The apparatus of claim 2, wherein the forming tool includes a linear slide for translating one of the shafts in a direction perpendicular to the parallel axes and the displacement of the forming surfaces of the mandrels further includes translating one of the shafts and forming surface toward the other shaft and forming surface.

4. The apparatus of claim 3, further including motors coordinated by a programmable controller for rotating the shafts and translating the one shaft.

5. The apparatus of claim 1, wherein the two dimensional wire includes alternating arcuate cusps and commissure tips, and the clamps and mandrels cooperate to hold two of the commissure tips with one of the arcuate cusps therebetween, the forming surfaces therefore bending the arcuate cusp of the wire when displaced.

6. The apparatus of claim 5, wherein each clamp and mandrel is disposed on a shaft, and either the mandrel or clamp is arranged to slide along the shaft with respect to the other to alternately hold and release the wire between the clamp and mandrel.

7. The apparatus of claim 6, wherein the two dimensional wire includes alternating arcuate cusps and commissure tips, and each mandrel includes a channel and cross-bores opening to the channel, each clamp including a recess aligned with the channel, wherein a pair of pins are provided fitting in the crossbores and sized so that one of the commissure tips may be wrapped therearound, the pins projecting into the channel a distance that permits sliding of the mandrel into cooperation with the clamp such that the projections of the pins fit within the clamp recess and the commissure tip is retained between the channel and recess.

8. A subassembly for bending a wire for a heart valve wireform, the wireform having alternating arcuate cusps and arcuate commissure tips, comprising:

a pair of mandrels having forming surfaces that have non-cylindrical cross-sectional shapes.

9. The subassembly of claim 8, wherein each mandrel includes a throughbore and a keyway, and further including, for each mandrel:

a shaft sized to fit within the throughbore having an axial groove; and a key sized to fit within the groove in the shaft and within the keyway and couple rotation of the shaft and mandrel.

10. The subassembly of claim 9, further including, for each mandrel, a clamp having a throughbore and a keyway sized to receive the shaft and key, respectively, and couple rotation of the shaft, mandrel and clamp.

11. The subassembly of claim 10, wherein each mandrel further includes an axial channel on one side adjacent the forming surface, and the clamp includes an external recess aligned with the channel, the subassembly further including a retaining pin projecting into the channel and sized to receive therearound one of the arcuate commissure tips of the two-dimensional wire, the commissure tip being retained by overlapping of the channel and recess.

12. A method for forming a three-dimensional wireform for use in a heart valve, comprising:

bending a wire into a flat (2-dimensional) undulating pattern of the alternating cusps and commissures; and bending the flat pattern into a three dimensional shape using:

a pair of mandrels having forming surfaces that have non-cylindrical cross-sectional shapes.

13. The method of claim 12, further including:

providing a forming tool having clamps for cooperating with the mandrels and rigidly holding a two-dimensional wire;

displacing the forming surfaces of the mandrels with respect to one another to bend the wire into a three-dimensional shape.

14. The method of claim 13, wherein the forming tool includes first and second shafts arranged to rotate along parallel axes, the mandrels including throughbores sized to receive the respective shafts, and further including rotating the shafts to cause the displacement of the forming surfaces of the mandrels.

15. The method of claim 14, wherein the forming tool includes a linear slide for translating one of the shafts in a direction perpendicular to the parallel axes and the displacement of the forming surfaces of the mandrels further includes:

translating one of the shafts and forming surface toward the other shaft and forming surface.

16. The method of claim 15, further including:

coordinating the rotation of the shafts and translation of the one shaft using motors and a programmable controller.

17. The method of claim 12, further including:

holding two of the commissures of the wire with a cusp therebetween and using the pair of mandrels to bend one cusp at a time.

* * * * *